United States Patent [19]
Nakatani et al.

[11] 3,963,348
[45] June 15, 1976

[54] DEVICE FOR DETECTING STRAIN AND FOREIGN MATTERS IN GLASS CONTAINER BY A NON-STORAGE TYPE PICKUP TUBE

[75] Inventors: Satoshi Nakatani, Nishinomiya; Yoichi Ito, Amagasaki, both of Japan

[73] Assignee: Yamamura Glass Kabushiki Kaisha, Japan

[22] Filed: June 5, 1975

[21] Appl. No.: 584,047

Related U.S. Application Data

[63] Continuation-in-part of Ser. No. 379,393, July 16, 1973, abandoned.

[30] Foreign Application Priority Data

July 14, 1972 Japan................................ 47-71058
Mar. 29, 1973 Japan................................ 48-36464

[52] U.S. Cl. ........................... 356/33; 209/111.7 T; 250/223 B; 250/225; 356/114; 356/197; 356/198; 356/240
[51] Int. Cl.² ................. G01B 11/18; G01N 21/04; G01N 21/16
[58] Field of Search ............. 356/33, 114, 119, 197, 356/198, 240; 250/225, 223 B; 209/111.7

[56] References Cited
UNITED STATES PATENTS

| | | | |
|---|---|---|---|
| 1,934,187 | 11/1933 | Glasgow et al. | 356/33 |
| 2,073,691 | 3/1937 | Gray | 356/33 |
| 2,509,068 | 5/1950 | McMahon | 250/225 |
| 2,798,605 | 7/1957 | Richards | 356/240 |
| 3,351,198 | 11/1967 | Wyman | 356/240 |
| 3,456,788 | 7/1969 | Stape et al. | 356/240 |
| 3,656,854 | 4/1972 | Bricker et al. | 356/119 |

*Primary Examiner*—Vincent P. McGraw
*Attorney, Agent, or Firm*—Holman & Stern

[57] ABSTRACT

A device for detecting a strain and foreign matters in a glass container is designed to amplify the electrical output obtained by bringing vertical scanning lines into intersection with the image of horizontally rotating strain polarized light. A polarizer and an analyzer are disposed in such a manner that their optical axes cross each other at right angles, and polarized light from the polarizer is projected upon a rotating glass container under inspection and is allowed to pass through the analyzer only when strain and/or foreign matter is found in the glass container. The resulting strain polarized light is projected upon a non-storage camera tube through a lens so as to vertically scan with a line through the center of an image of the glass container on the photoelectric surface of the tube at a speed proportional to the moving speed of the glass container to thereby bring the vertical scanning lines into intersection with the image of the horizontally rotating strain polarized light.

9 Claims, 7 Drawing Figures

DEVICE FOR DETECTING STRAIN AND FOREIGN MATTERS IN GLASS CONTAINER BY A NON-STORAGE TYPE PICKUP TUBE

RELATED CASE

This application is a continuation-in-part of application Ser. No. 379,393 filed July 16, 1973 now abandoned.

BACKGROUND OF THE INVENTION

When foreign matter becomes mixed into a glass body or when flaws in glass quality are brought about by changes due to heat, a so-called strain is produced in a container made of such glass material, with the result that the glass container is greatly reduced in quality. When a glass bottle having strain is used, for example, as a container for beverages, there is a possibility of the bottle being broken during use because of the strain, and particularly when such a glass bottle is used as a container subject to internal pressure, such a possibility is immensely increased. Also, when bubbles are produced in the glass of a glass container, the container is reduced in quality and strength.

In detecting foreign matter in a glass bottle, macrography by an examiner has heretofore been a general practice which however has various disadvantages such as lack of efficiency, variation in precision in examination due to a difference between examiners, reduced precision in examination, etc.

Although there exists automatic optical testers as a means for detecting foreign matter that has gotten mixed into the glass of a glass bottle, testers of this kind have the disadvantage that when the foreign matter is transparent or translucent or when an object to be examined such as a glass bottle is impressed with letters and characters in the form of, for example, raised letters, the irregular reflection and light-screening effects resulting therefrom act as a deterrent to detection of strain.

Known prior art in determining the quality of a glass bottle by an electric signal into which an optical state of the bottle is converted by use of a camera pickup tube includes Japanese Patent Publication No. 9998/1973. However, the art described therein requires a plurality of reflecting optical systems, does not provide sufficient monitoring, and also renders it difficult to make a speedy examination of a large number of bottles.

Devices using TV apparatuses are also known in the art. Generally, they all employ storage type pickup tubes and detect irregularities in glass by TV scanning immediately after temporarily storing (by means of an on-and-off light source like a flash lamp) a stationary image of only one side of an object on the photoelectric surface of a pickup tube. Thus, in order to examine the whole circumferential surface of an object, a plurality of TV cameras must be used in conjunction with a complicated control mechanism. Further, linear scanning and the following of an object at an optional speed, as used in this invention, are practically impossible by a storage type pickup tube due to the risk of burnt photoelectric surfaces or residual images.

Related prior art U.S. patents of which we are aware include Glasgow et al U.S. Pat. No. 1,934,187; Gray U.S. Pat. No. 2,073,691; Richards U.S. Pat. No. 2,798,605; and Wyman U.S. Pat. No.3,351,198. Each of the devices described in the foregoing patents, however, is subject to certain deficiencies which render the glass defect detecting apparatus therein described either inaccurate or imprecise. The Gray patent, for example, relies upon human visual observation for a readout, while the Glasgow et al patent is exemplary of a single-sided observation detection scheme, as discussed above. Further, the Richards patent provides no means for either synchronizing the movement of the object under inspection with the scanning lines, nor for ensuring that the entire surface of the object is inspected thoroughly and completely.

SUMMARY OF THE INVENTION

This invention relates to a device for detecting strain and foreign matter in a glass container and more particularly to a device for detecting not only strain and/or foreign matter in the glass of a glass container but also foreign matter within the container and on the surfaces thereof, when foreign matter gets mixed into the glass of the bottle or a strain is produced in the glass of the bottle by defective heat treatment and/or bubbles are produced in the glass during a stage of manufacture of the bottle and when foreign matter gets inadvertently slipped into the bottle or attached to the glass of the bottle.

A primary object of this invention is to provide a device for accurately detecting strain, foreign matter, and/or bubbles existing in the glass of a glass container described above, even when the glass container is impressed with letters, symbols or the like.

Another object of this invention is to examine glass containers one by one precisely and efficiently in ascertaining the quality of a glass container from the optical state of the strain and foreign matter.

A further broad object of this invention is to be able to include the following cases in which the device of this invention may be used for detecting the strain in the glass of a glass bottle and foreign matter in the bottle: (A) the case in which optically anisotropic crystals exist in the glass of a bottle and a birefringent phenomenon is present; (B) the case in which there exist bubbles in the glass; (C) the case in which foreign matter exists inside the glass bottle or foreign matter is attached to the inner and outer walls of the bottle; and (D) the case in which foreign matter gets mixed into the liquid capable of easily passing light therethrough. Such foreign matter is intended to include the following substances: (a) photoelastic substances such as plastic film and cellophane; (b) substances such as straw and paper which present a light scattering phenomenon; (c) optically anisotropic substances such as paper, cotton, or synthetic fibers; (d) a substance such as metal in which surface reflection presents an oval polarization phenomenon; and (e) a substance such as glass which presents an oval polarization phenomenon.

A further object of this invention is to provide a device for automatically and continuously examining a glass container according to the above principles, said device including means for bringing the glass container continuously and automatically supplied into rotation on its own axis in an examination station, means for moving the glass container placed thereon within the station in the same direction as that in which the glass is rotated, and means for selectively transferring the glass containers which pass the examination to the next step of the process.

Another object of this invention is to provide an effective combination of a mechanism for mechanically rotating an object to be examined with a novel TV linear scanning technique to thereby eliminate all problems met in the prior art devices discussed above.

The foregoing and other objects are attained in accordance with a preferred embodiment of the present invention through the provision of a device for detecting strain and foreign matter in a glass container which is designed to amplify the electrical output obtained by bringing vertical scanning lines into intersection with an image of horizontally rotating strain polarized light. An analyzer and a polarizer are disposed on opposite sides of a glass container to be examined such that their optical axes intersect at right angles. Polarized light from the polarizer is projected upon the rotating glass container and is allowed to pass through the analyzer only when strain and/or foreign matter is found therein. The resultant strain polarized light is projected upon a non-storage camera tube through a lens so as to vertically scan one line through the center of an image of the glass container on the photoelectric surface of the tube in synchronism with the moving speed of the glass container, thereby bringing the vertical scanning line into intersection with the image of the horizontally rotating strain polarized light.

BRIEF DESCRIPTION OF THE DRAWINGS

Other objects, advantages and features of this invention will become more apparent from the detailed description of the present invention when taken in conjunction with the accompanying drawings, in which.

DETAILED DESCRIPTION OF THE PREFERRED EMBODIMENT

Figure 1:
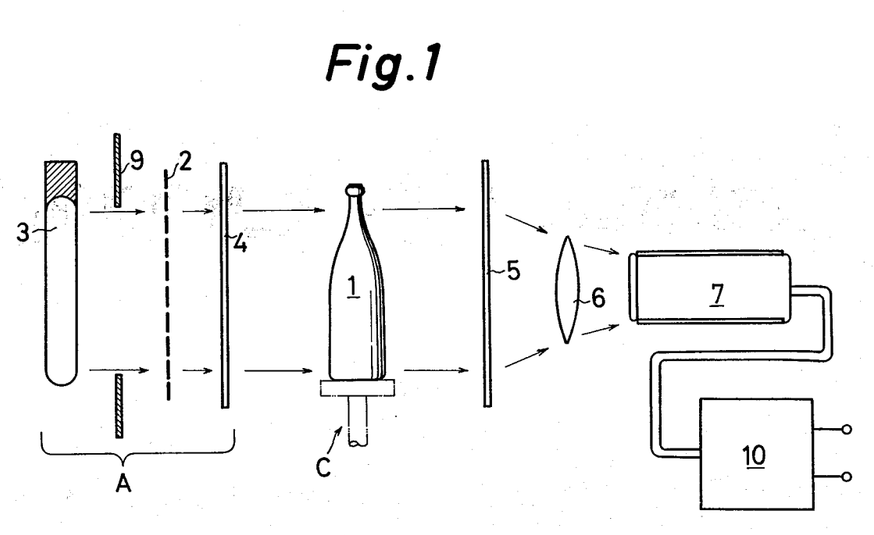
FIG. 1 is a diagrammatic view of an embodiment of this invention.
Figure 3:
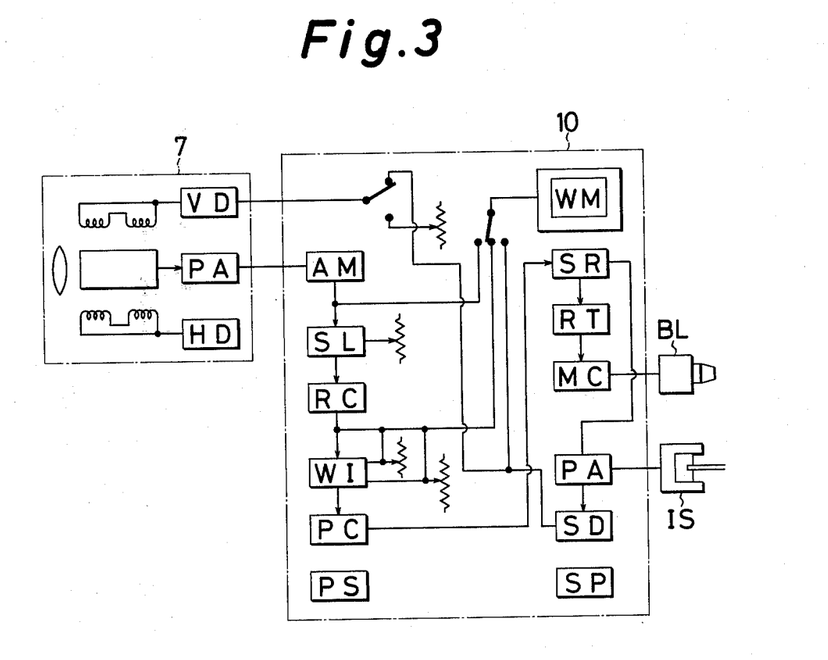
FIG. 3 is a block diagram of an electrical detection system according to the present invention.

Referring now to the drawings, the numeral 1 designates a glass bottle in the form of an object to be examined; A designates a light source means for generally projecting polarized light in a direction indicated by the arrows; 2 a filter that screens ultraviolet and infrared rays from a light source 3 and passes visible light alone; 4 a polarizer that passes only vibration in one direction of the light mentioned above; and 5 designates an analyzer located in opposed relation with respect to said polarizer on the light path along which the polarized light which passed through the polarizer 4 travels through the central axis of the bottle 1. The polarizer 4 and analyzer 5 are disposed in a relation in which their optical axes intersect each other at right angles. The numeral 6 designates a lens; and 7 designates a non-storage camera tube, which is disposed in such a manner that the polarized light which passes through the analyzer 5 may focus through the lens 6 into an image on the photoelectric surface of the camera tube 7. The character C designates a rotating means for turning the glass bottle 1 about its longitudinal axis and 9 designates a vertical slit in the light source means. The numeral 10 designates a signal processing system, which includes, as seen in FIG. 3, a camera control circuit including an amplifying unit AM connected to a preamplifier PA of the camera pickup tube 7, slicer SL, integrator RC, width detector WI and pulse former PC, and a defective bottle rejecting circuit 11 including a wave-form monitor WM and shift register SR and others associated with said control circuit. The character RT designates a rejecting timer; MC a magnet value regulator; CA a pulse amplifier; SD a scanning positioning synchronous circuit connected to a transverse deflecting coil of the camera pickup tube and a signal indicating the speed of movement of the glass bottle; PS a power source; SP a stabilizing power source; BL a blower for rejecting a defective bottle; and IS designates an examination starting signaller.

In the structure above, light from a power source 3 passes through a slit 9 and is projected on a filter 2, but the filter 2 screens ultraviolet rays and infrared rays and permits only visible light to pass therethrough and to be projected on a polarizer 4 which projects only vibration in one direction of the light on a bottle 1 in the form of an object to be examined.

When there is no strain and/or bubbles and/or foreign matter existing in the bottle 1, the polarized light from the polarizer 4 passes through the bottle 1 and reaches the analyzer 5, but since the analyzer 5 is disposed in such a relation that the optical axis of the analyzer 5 intersects at right angles with the optical axis of the polarizer 4, it does not permit that polarized light from the polarizer 4 which passes through the bottle 1 to transmit through the analyzer 5. On the other hand, the camera pickup tube 7 is disposed in such a manner that an image of the bottle 1 is thrown into focus on the photoelectric surface of the tube 7 and scans the central axis of the image vertically. However, unless the analyzer 5 permits the light from the bottle 1 to pass therethrough, the camera pickup tube 7 will not change its electric output. Accordingly, the signal processing system 10 connected to the tube 7 will not operate.

Figure 2:
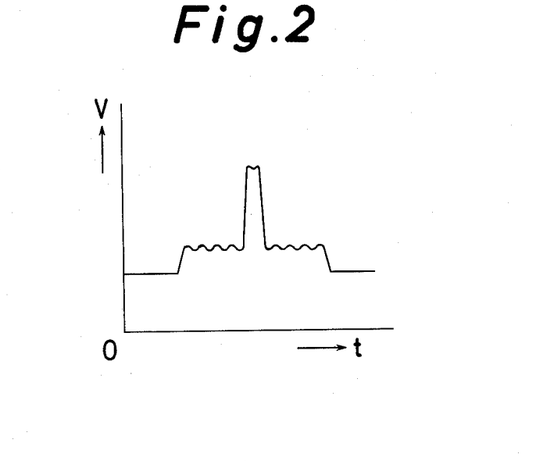
FIG. 2 is a diagram showing a wave-form obtained by converting the polarized light from the analyzer into voltage.

In contrast thereto, when there exists in the glass of the bottle 1 any strain and/or bubbles due to any foreign matter, the polarized light from the polarizer 4 passes through the analyzer 5 because of the change brought about in the direction of vibration of the polarized light by the optical property of the foregin matter. The polarized light that has thus passed reaches the photoelectric surface of the tube 7 through the lens 6. As previously described, because the bottle 1 is rotating on a rotating device C, that polarized light resulting from said strain which is transmitted through the analyzer 5 travels horizontally. Accordingly, the vertical scanning lines of the pickup tube 7 will intersect said horizontally travelling polarized light, and as shown in FIG. 2, the pickup tube 7 obtains an output signal resulting from the photoelectric conversion effect of the image formation face of the tube 7. Two low waveforms in FIG. 2 indicate an output resulting from other than the foreign matter of the bottle 1. This electric output is amplified by the control system shown in FIG. 3, and a defect indicating signal is obtained in a width detector WI which is connected to a defective bottle rejecting circuit 11. An air rejector BL is operated at a specified time when the detected defective bottle is moving along its path, and the defective bottle is removed from the chain of bottle conveyors.

It is notable that the device of the present invention utilizes a non-storage type pickup tube, the horizontal scanning signal of which is produced by a signal from a sine wave oscillator, while the vertical scanning signal is produced by a signal proportional to the speed of movement of the container under inspection. More specifically, the pickup tube according to the present invention is rotated 90° with respect to the customary orientation thereof, i.e., the horizontal scan HD effects longitudinal scanning of the object, i.e., scanning along the central axis of the object in a vertical direction, while the vertical scan HD effects transverse scanning of the object. The horizontal scan of the tube thus effects linear 1-dimensional longitudinal scanning of the object to be inspected and is set to scan along the center line of the object. When the object is in continuous transverse motion, the longitudinal scanning of the rotating object is accomplished in accordance with and so as to follow the transverse movement of the object. That is, the longitudinal scanning line generated through HD is positioned to follow the transverse movement of the object by a signal from SD through switch SS as shown, the signal corresponding to the moving speed of movement of the object, to thereby ensure that the entire object is inspected thoroughly and completely. As is also illustrated, the other position of switch SS taps a potential from variable resistor VP which serves to fix the position of the longitudinal scan when the object is not transversely moving but is only rotating.

Thus, linear scanning, which means to scan only one line on the photoelectric surface of a pickup tube, is effectuated. In the present invention, with the use of a non-storage type pickup tube such as an image dissector, the rotating image of an object such as a glass bottle is formed on the photoelectric surface of the pickup tube, and the center of the image is scanned only along one line in the direction of the rotational axis of the glass bottle. Thus, the entire circumferential surface of the object is effectively examined continuously without being affected by diffused light reflection.

Figure 7:
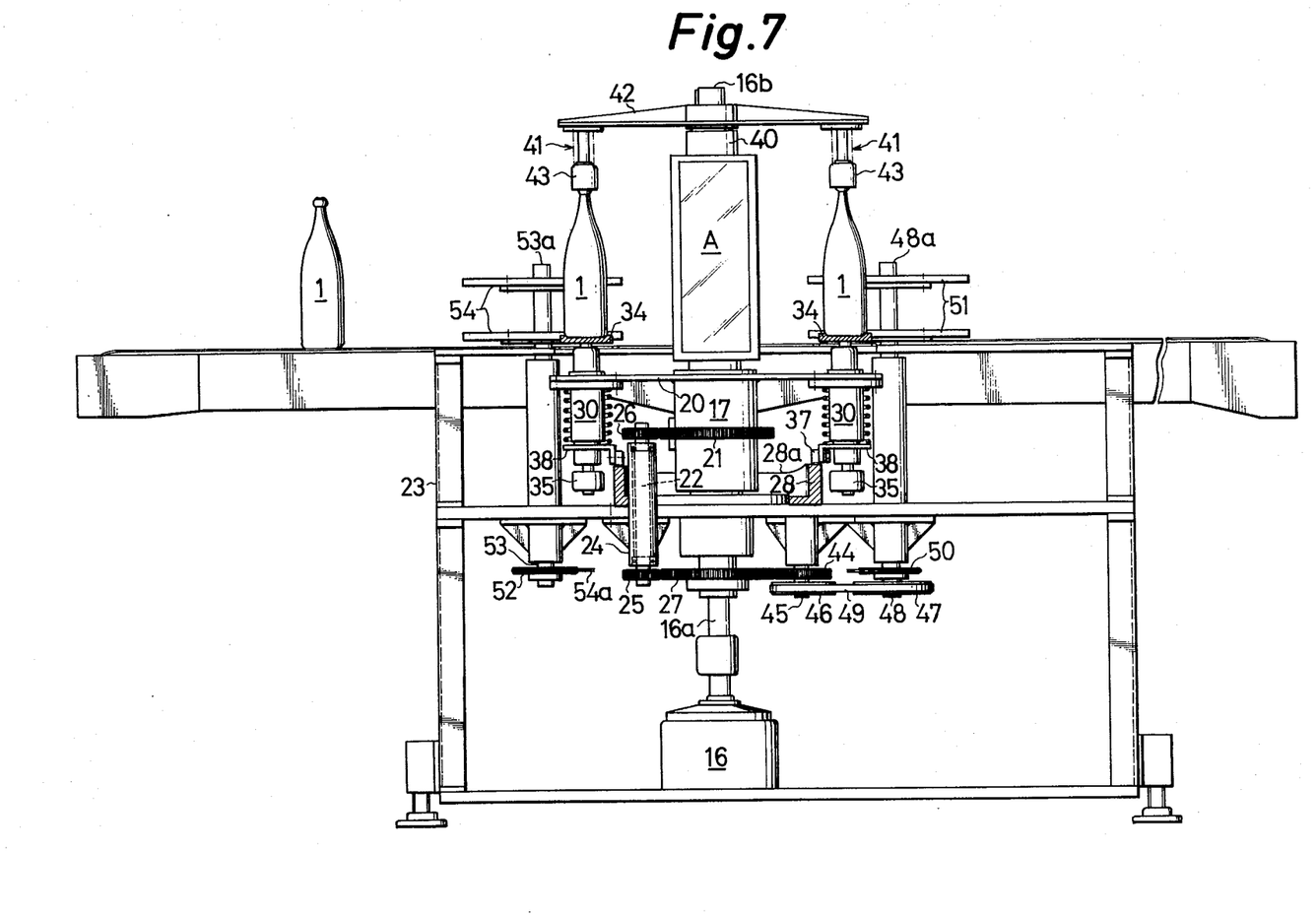
FIG. 7 is a front view of FIG. 4.

A description will now be made of an embodiment of an automatic device for continuously examining the existence of the strain and/or foreign matters described above in a number of bottles. In FIGS. 4 through 7, the numeral 16 designates a reduction geared motor and its driving shaft 16a is vertically held within a sleeve 40 fixed on a frame 23. The numeral 17 designates a cylindrical member rotatably mounted around the sleeve 40 through bearings 18 and 19, and on the upper periphery of the cylindrical member 17 is horizontally mounted a disclike rotary member 20 and on the periphery of the cylindrical member 17 is mounted a driven gear 21. In FIG. 7, the numeral 22 designates a shaft rotatably provided in a cylinder 24 fixed to the frame 23, and to the upper and lower ends extending from the cylinder 24 of the shaft 22 are attached a first intermediate gear 25 and a second intermediate gear 26, said first gear 25 meshing with a driving gear 27 mounted on a driving shaft 16a and said second gear 26 meshing with the driven gear 21. The numeral 28 designates a circular cam fixed to the frame 23, and the upper end of the circular cam 28 is formed into a cam face 28a and positioned concyclically around the driving shaft 16. To the horizontally provided rotary member 20 are fixed a plurality of outer cylinders 30 at equal spaces apart from each other concyclically of the member 20. On the upper and lower sides of the inner cylinder 31 vertically slidably inserted into each of said outer cylinders 30 is rotatably mounted a rotary shaft 29 through bearings 32 and 33. At the upper end of the rotary shaft 29 is a disc 34 for rotating a bottle 1 to be examined, and at the lower end thereof is mounted a rotor 35. The numeral 36 designates a guide provided peripherally of the inner cylinder 31, the guide extending into a longitudinal groove 30a of the outer cylinder 30 and being adapted to guide up-and-down movement of the inner cylinder 31. On the lower periphery of the inner cylinder 31 is fixed a driving member 38 having rollers 37. The rollers roll on the cam face 28a of the circular cam 28. The driving member 38 is loaded with a spring 39 from the outer cylinder 30 so as to allow the rollers 37 to roll into contact with the cam face 28a of the cam 28. The numeral 41 designates a mouthpiece unit, which is made up of a mouthpiece holding member 42 attached to the top portion 16b of the driving shaft 16a and rotatable with the top portion 16b and a mouthpiece 43 depending from the underside of the holding member 42. The mouthpiece 43 is provided in plural numbers, and such mouthpieces are equally spaced apart and concyclically around the driving shaft 16a. The lower opening of the mouthpiece 43 is located on the same centerline as the bottle rotating disc 34 and is so constructed as to hold the mouth of a glass bottle (an object 1 to be examined) by the upward movement of the rotating disc 34. The numeral 44 designates a gear which is mounted on the shaft 45 rotatably mounted on the frame 23 and which is meshable with a gear 27 on the driving shaft 16a. A pulley 46 is mounted coaxially with the gear 44. The pulley 46 transmits rotation of the driving shaft 16a through a belt 49 to another pulley 47 mounted on a shaft 48 rotatably attached to the frame 23. On the shaft 48 of this pulley 47 is mounted a sprocket wheel 50 and the upper end 48a of the shaft 48 extends to a part of a bottle conveying means (to be later described) on the frame 23, to which part is attached a star wheel 51 for automatically feeding bottles 1. The numeral 52 designates a sprocket wheel provided in the lower part of a rotatable shaft 53 supported on the frame 23 and which is movable in cooperation with the sprocket wheel 50 through a chain 54a. The upper part 53a of the shaft 53 extends upwardly of the frame 23, and on the upper part 53a is mounted a star wheel 54 for feeding bottles 1 at equal spaces apart from each other. The numerals 55 and 56 designate star wheel guides, the guide 55 being adapted to guide the bottles 1 which are fed by the feeding star wheel 54 one after another onto the rotating discs 34, while the guide 56 being adapted to guide the examined bottles 1 to the feeding star wheel 51. The numeral 57 designates a bottle feed conveyor; 58 a side guide for the conveyor 57; 59 a table connected to said conveyor 57; and 60 designates a screw for feeding the bottles 1 supplied onto the table to the feeding star wheel 54, the screw 60 being operated through a final drive gear reduction 61. The numeral 62 designates a bottle delivery conveyor; 63 a side guide for the conveyor 62; 64 a defective bottle rejecting gateway formed on the delivery path for bottles 1; and 65 designates a rejecting means that jets compressed air, the rejecting means 65 jetting a specified amount of compressed air by an operation instruction signal given through a reject timer RT in the defective bottle rejecting circuit 11 shown in FIG. 3, and rejecting a defective bottle through the gateway 64.

A first pulley 67 is mounted on the end of a driving shaft 66a of a motor 66 that imparts rotation to the bottle 1 and another pulley 68 is mounted on the frame 23, and both pulleys are spanned with a belt 69. One path for the belt 69 is disposed in such a manner that a rotor 35 at the lower end of the rotating shaft 29 inside the outer cylinder 30 supported on the rotary member 20 intersects tangentially for a certain time the locus the rotator described in its travelling around the driving shaft 16a.

Figure 4:
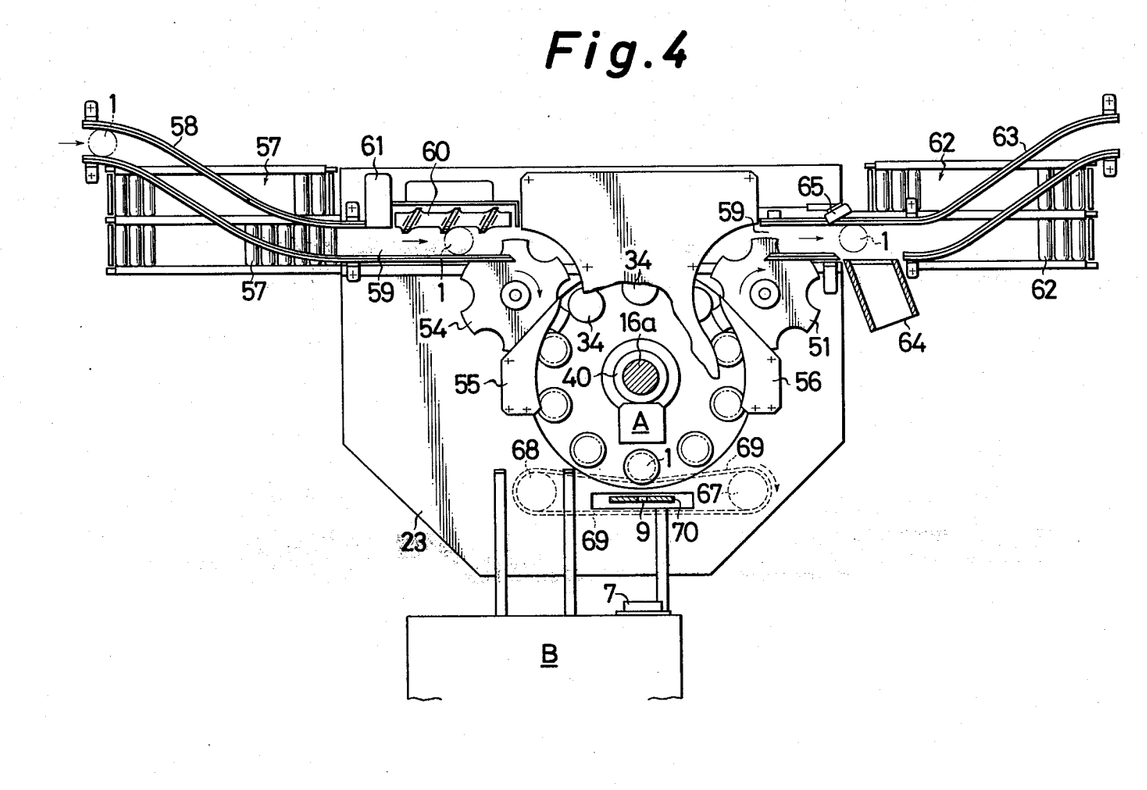
FIG. 4 is a plan view, broken in part, showing the essential parts of an automatic continuous examination device according to the present invention.
Figure 5:
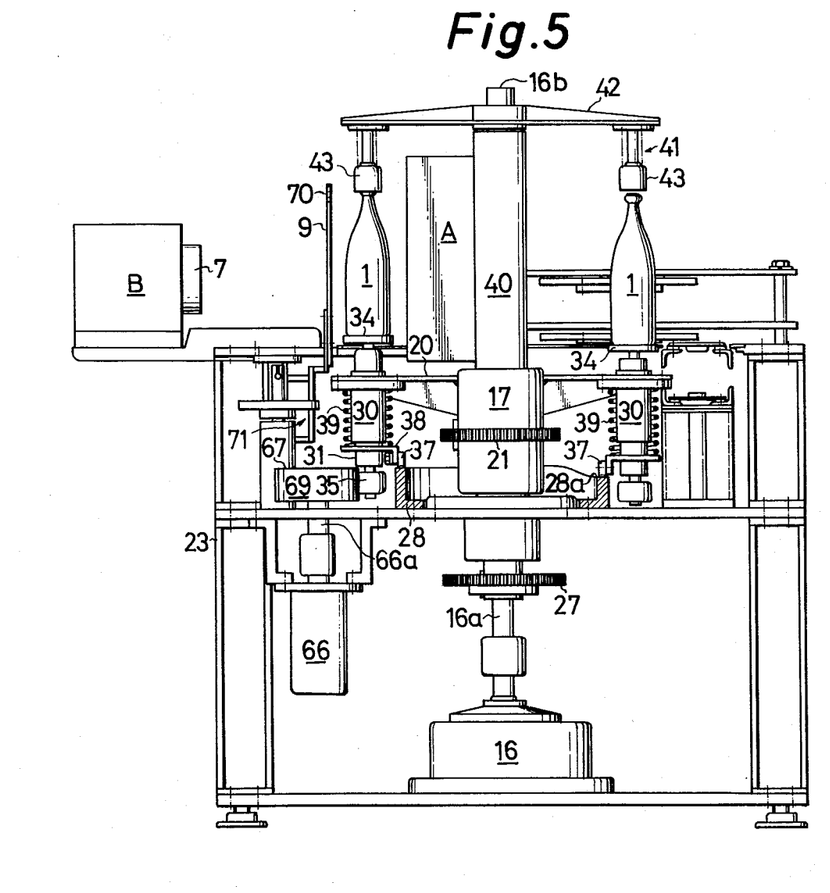
FIG. 5 is a side view of FIG. 4 being partly broken away for clarity.
Figure 6:
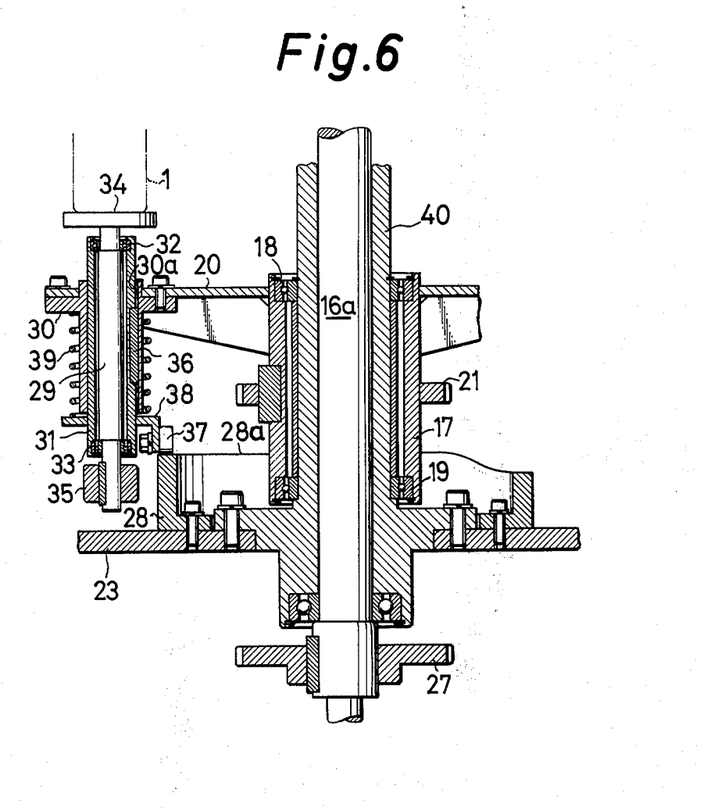
FIG. 6 is a longitudinal sectional view showing the essential parts of the device seen in FIG. 5.

A projection device A in FIG. 1 including a light source 3, filter 2 and polarizer 4 is mounted on a part of fixed sleeve 40 in FIG. 4. The camera pickup tube 7 having the analyzer provided in front of its light receiving face is disposed on the frame 23 in front of the projection device A. The path for the rotary disc 34 for the bottle 1 lies between the device A and the tube 7. In the embodiment illustrated, a slit 9 is located in front of the tube 7, and a slit plate 70 which forms the slit 9 and with which a crank mechanism 71 is associated is constructed so as to be able to examine a bottle 1 being revolved by a driving mechanism (not shown) from a driving gear 27 mounted on a driving shaft 16a of a motor 16 in such a manner that the slit plate moves forth in attendance on revolution of the rotary disc 34 for the bottle 1 around the shaft 36 and, upon completion of examination, moves back immediately to its original position. The camera pickup tube 7, signal processing system 10, and defect rejecting circuit 11 are received in device B in the embodiment described in FIG. 4 and those that follow.

A description will now be made of operation of the embodiment of the invention.

A bottle 1 fed by a guide 58 onto a conveyor 57 is transported on a table 59 to a guide element of a star wheel 54 by the action of a screw 60, and is placed by rotation of the star wheel 54 onto a bottle turning rotary disc 34 that is continuously rotating in connection with the star wheel 54. A plurality of rotating shafts 29 mounted concyclically of a rotary member 20 rotated by rotation of the driving shaft 16a of a motor 16 are not moved upward but are in their lower positions when rollers 39 secured to an inner cylinder 31 are positioned on the lower end face of a circular cam 28, and accordingly the bottle 1 is kept away from a mouthpiece 43 at the point of time at which the bottle has been supplied from the feeding star wheel 54, but when the rollers 37 are moved up to the upper end face of the circular cam 28 by rotation of the rotary member 20, the bottle 1 with its mouth put into the mouthpiece 43 is clamped between the mouthpiece 43 and the rotary disc 34. When the bottle 1 is moved in front of a camera pickup tube 7 by rotation of the rotary member 20, a rotor 35 at the lower end of the rotating shaft 29 is frictionally rotated by the rotor 35 being brought into contact with one run of a belt 69 rotated by a motor 66 and pulleys 67 and 68. Accordingly, the rotary disc 34 also turns on its own axis. In synchronism with the revolution of the rotary member 20 accompanied by the turning of or disc 34 on its own axis, a slit 9 is moved. The slit is adapted to screen light that hinders detection and has much to do with the life of the camera pickup tube, but this may be dispensed with by reducing the width of the scanning lines of the pickup tube. Projection from a projection device A by use of a polarizer 4 is made throughout the bottle and if there should be strain and/or foreign matter in the bottle 1, the bottle transmitted light that has optically been changed in its direction of vibration by the strain of the foreign matter passes through an analyzer 5 and, because the bottle 1 is being rotated at this time, the bottle 1 is imaged as a horizontally moving luminous body on the photoelectric surface of the pickup tube 7, intersects the vertical scanning lines and imparts an output to a signal processing system connected to the pickup tube 7.

The bottle 1 that passed in front of the tube 7 is revolved and moved toward a star wheel 51. During this movement, the rollers 37 attached to an inner cylinder 31 are again positioned on the lower end face of the circular cam 28, and accordingly the rotary disc 34 is moved downward and the mouth of the bottle 1 is separated from the mouthpiece 43. The bottle 1 on the rotary disc 34 while being guided by rotation of the feeding star wheel 51, is transferred onto a delivery table 59, but when the pickup tube 7 has detected a defected bottle on the table 59, a reject device 65 that receives a signal from the signal processing system jets compressed air upon receipt of the operation signal given through a reject timer, with the result that the defective bottle 1 is rejected to a defect rejecting gateway 64 by the compressed air.

A bottle 1 having no strain and/or foreign matter, while being guided by a conveyor 62 and its guide 63, is transferred to the next station. Breakage of glassware, especially of an article subject to internal pressure, is due to the existence of strain and bubbles in the article. A defective article rejected by this examination and an article that passed the examination were subjected to an internal pressure test and the resulting mean breaking pressure of the two kinds of articles were as follows:

| Article | Defective bottle mean breaking pressure (kg/cm$^2$) | Passed bottle mean load pressure (kg/cm$^2$) |
| --- | --- | --- |
| 633 cc beer bottle | 18.3 | 29.2 |
| 500 cc carbonated beverage bottle | 25.4 | 37.5 |

According to this invention, as mentioned above, since raised letters such as trademark, patterns, or symbols formed on the bottle are put to examination by vertically scanning the center position of the bottle, there is no light that is incident from the analyzer upon the camera pickup tube and accordingly, any electric output by the incident light will appear in the form of a constant wave-form (like the two low portions of the wave-form in FIG. 2) and the wave-form is distinguishable from an unusual wave-form resulting from strain and/or foreign matter, and hence this invention can be applied to various glass containers, with the advantage of accurate results being obtainable.

It should be understood that the embodiment of the continuous examination device according to the invention described and illustrated in FIG. 4 and those that followed is given by way of example to show one of a possible designs and that numerous other embodiments and modifications may be made of the invention without departing from the scope and spirit of the invention.

What is claimed is:

1. A device for detecting strain and foreign matter in a glass container, comprising:

means for moving a glass container;
a light source located on one side of the glass container placed and moving means;
a polarizer transmittting vibration only in one direction of light from said light source and located between the light source and the glass container;
an analyzer placed on the other side of the glass container so that the optical axis of the analyzer intersects that of the polarizer at right angles;
means for rotating said glass container on said moving means.
a non-storage type pickup tube for receiving on a photoelectric surface thereof an image of the glass container placed on said moving means;
position detecting means for detecting from said moving and feed means the position and speed of the glass container;
said non-storage type pickup tube being provided so that the image on the photoelectric surface thereof of the glass container in rotational movement is always scanned along the center line in a longitudinal direction in synchronism with the speed of movement of the glass container, whereby:
an abnormal electrical output of the image of the glass container due to light depolarized by foreign matter in the glass container and double deflection caused by strain in the glass container is detected from a constant electrical output of the image changed photoelectrically by the non-storage type pickup tube to thus ensure the rejection of a defective glass container.

2. The device for detecting strain and foreign matter in a glass container as set forth in claim 1, further comprising:
rotary table means having glass container rotating discs radially disposed thereon;
continuous glass container feed means and a continuous glass container delivery means connected tangentially to said rotary table means;
glass container feed means disposed between the continuous feed means and the glass container rotating discs on the rotary table means and comprising a star wheel and a guide;
polarized light projecting means including a light source for the glass containers on the glass container rotating discs and a polarizer;
said non-storage type pickup tube including an analyzer for receiving a polarized light image of the glass container passing in front of said polarized light projecting means; and
electrical detecting means electrically connected to the non-storage type pickup tube.

3. The device for detecting strain and foreign matter in a glass container according to claim 2 wherein a friction belt means horizontally driven below said rotary table means and a roller in contact with one run of said friction belt means are fixed to the lower end of the rotating shaft of said glass container rotating discs.

4. The device for detecting strain and foreign matter in a glass container according to claim 2 wherein examination means connected to said pickup tube includes an amplifier of the output of the pickup tube, a differential amplifier, an abnormal signal decision circuit and its memory unit and signal processing system.

5. The device for detecting strain and foreign matter in a glass container according to claim 4 wherein said abnormal signal memory unit includes a timer for rejecting a glass bottle having strain and foreign matter in the glass thereof and a magnet valve regulator controlled by said timer.

6. The device for detecting strain and foreign matter in a glass container according to claim 5 wherein a bottle rejecting means controlled by said magnet value regulator is disposed in part of the glass container delivery means.

7. A device for detecting strain and foreign matters in a glass container using a non-storage type pickup tube, comprising:
means for rotating a glass container;
a light source located on one side of said glass container positioned on said rotating means;
polarizer means located between said light source and said glass container for transmitting vibration only in one direction of visible light from said light source;
an analyzer placed on the other side of said glass container with the optical axis thereof crossing that of said polarizer at right angles;
a non-storage type pickup tube placed along the optical axis of said analyzer for scanning an image of said glass container vertically in the direction of the rotational axis of said glass container;
signal processing means for processing the output of said pickup tube; and
electrical positioning means capable of selectively fixing the scanning line position in said pickup tube,
whereby an image of said glass container is formed on the photoelectric surface of said pickup tube and only the center line of the image is scanned vertically in a corresponding direction to thereby detect strain and foreign matters in said glass container.

8. The device for detecting strain and foreign matter in a glass container according to claim 7 wherein examination means connected to said pickup tube includes an amplifier of the output of the pickup tube, a differential amplifier, an abnormal signal decision circuit and its memory unit and signal processing system.

9. The device for detecting strain and foreign matter in a glass container according to claim 8 wherein said abnormal signal memory unit includes a timer for rejecting a glass bottle having strain and foreign matter in the glass thereof and a magnet valve regulator controlled by said timer.

* * * * *